Figure 1:
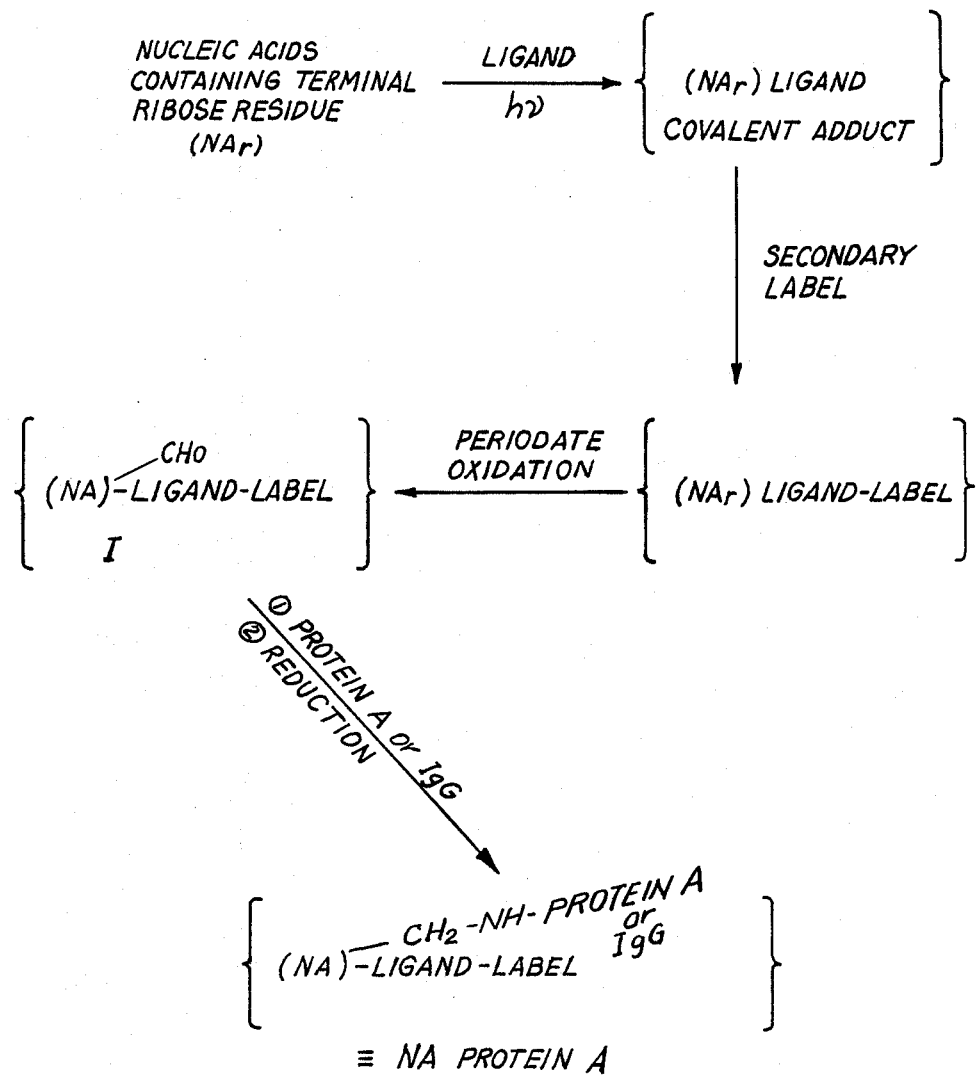

United States Patent [19]

Dattagupta et al.

[11] Patent Number: 4,748,111
[45] Date of Patent: May 31, 1988

[54] NUCLEIC ACID-PROTEIN CONJUGATE USED IN IMMUNOASSAY

[75] Inventors: Nanibhushan Dattagupta, New Haven; William J. Knowles, Hamden; Vincent T. Marchesi, Guilford; Donald M. Crothers, Northford, all of Conn.

[73] Assignee: Molecular Diagnostics, Inc., West Haven, Conn.

[21] Appl. No.: 588,858

[22] Filed: Mar. 12, 1984

[51] Int. Cl.$^4$ .................... G01N 53/00; G01N 33/53; G01N 33/543; C12Q 1/68
[52] U.S. Cl. ........................... 435/7; 435/6; 436/547; 436/828; 436/518; 530/402
[58] Field of Search ............... 260/112 R; 435/7, 174, 435/6; 436/518, 547, 828; 530/402, 358

[56] References Cited

U.S. PATENT DOCUMENTS

| | | | |
|---|---|---|---|
| 4,358,535 | 11/1982 | Falkow et al. | 435/5 |
| 4,469,787 | 9/1984 | Woods et al. | 435/7 |
| 4,587,044 | 5/1986 | Miller et al. | 435/6 X |

FOREIGN PATENT DOCUMENTS

0062892  4/1982  European Pat. Off. .

OTHER PUBLICATIONS

Chem. Abs. 86:151699m (1977), 87:129598b (1977), 91:189265h (1979), 91:87047w (1979).
Yamashita et al., J. of Virology, vol. 30, No. 2, p. 497–507, May 1979.
Coombs et al., Proc. Nat'l. Acad. Sci. U.S.A., vol. 75, No. 11, p. 5291–5295, Nov. 1978.
Mayo et al., J. Gen. Virology, vol. 43, p. 735–740, 1979.
Biol. Abs. 75(7):46643 (1983).
A. H. W. M. Schuurs & B. K. Van Weeman, *Clin. Chim. Acta*, 81, 1–40 (1977).

*Primary Examiner*—Esther M. Kepplinger
*Assistant Examiner*—Shawn P. Foley
*Attorney, Agent, or Firm*—Sprung Horn Kramer & Woods

[57] ABSTRACT

A protein is covalently coupled to a 3′terminal end of a nucleic acid which carries several labels. In an assay the protein will specifically recognize some component of a test system; in an immunoassay the protein can be Protein A which will recognize the FC portion of IgG which is bound to an unknown antigen if present in the test sample.

3 Claims, 2 Drawing Sheets

NUCLEIC ACID-PROTEIN CONJUGATE USED IN IMMUNOASSAY

The present invention relates to the labeling of proteins by covalently coupling them with labeled nucleic acids and the use of these labeled materials in immunoassays for diagnostic purposes, Immunological reagents, e.g., antibodies, are protein molecules that are produced by the body in response to the introduction of a fdreign substance known as an antigen. Specific antibodies bind to specific antigens creating antigen-antibody complexes. Since antibodies bind only to their complementary antigens, they can be used to detect the presence of specific antigens in different biological samples. Such immunological methods of detection and diagnosis of certain disease states have revolutionized the biomedical sciences. Antibodies are now routinely used to measure the presence of small quantities of special molecules (e.g., proteins, hormones, drugs) in blood, urine, and other body fluids.

One method commonly employed to detect the specific interaction between an antigen and its corresponding antibody is the radioimmunoassay (RIA), discovered by Yalow and Berson for the detection of insulin. (R. S. Yalow and S. A. Berson; *J. Clin. Invest.* 1960: 39: 1157–1175). RIA relies on the fact that the antigen being assayed is first labeled with a radioisotope and is then quantitated by standard means of counting radioisotopes. Each kind of radiolabeling has limitations, for example, sensitivity of detection, isotope half-life, hazard to the operator and the problem of waste disposal. The expense of the equipment necessary to count radioisotopes is also considerable. Therefore, it is highly desirable that immuno-labeling be accomplished without resort to radioactivity.

Although there are several nonradioactive immunoassay methods in practice, the level of sensitivity which can be reached by RIA has not been duplicated.

One type of assay, for example, is carried out by chemically treating antibodies with fluorescent compounds so that the location of the fluorescent-labeled antibody can be identified with the use of a special fluorescent microscope. The use of fluorescent-labeled antibodies is a widely used procedure with many applications, but this technique also has certain limitations, among them the fact that antibodies labeled by existing methods are not sensitive enough to detect small quantities of antigenic material. To increase sensitivity, polylysine has been used to couple fluorophores but high background problems are created because polylysine binds nonspecifically to many types of compounds.

Other types of labeling reagents include protein-bacteriophage conjugates, stable free radicals, electron dense compounds, luminescent compounds and enzymes. All of these labeling agents have certain disadvantages. Certain reagents, for example, enzymes, are difficult to store. Certain labeling reagents are not sensitive enough unless they are present in multiple copies. If multiple copies bf label are directly coupled to the reactants, as in the case of fluorescent label, the antibody may lose its capacity to bind to antigen, i.e., become less specific. [Review: A. H. W. M. Schuurs & B. K. Van Weemen, clin. chim. Acta 81, (1977) 1–40; D. S. Smith et al. Ann clin. Biochem. 18 (1981) 253–274]Therefore, it is highly desirable to label immunological reagents indirectly, to avoid such a decrease in specificity.

Application Ser. No. 513,932, filed July 14, 1983, now pending, the disclosure of which is incorporated herein by reference, discloses a photochemical method of labeling nucleic acids. The invention, preferably employed for detection purposes in hybridization assays, can be used in immunological assays. The labeling employs a photoreactive furocoumarin or phenanthridium compound to link the nucleic acid to a label which can be assayed in a conventional manner. The end product is thus a labeled nucleic acid probe comprising (a) a nucleic acid component, (b) a furocoumarin or phenanthridium compound photochemically linked to the nucleic acid component, and (c) a label chemically linked to (b). For coupling to DNA, aminomethyl trioxsalen, aminomethyl angelicin and amino alkyl ethidium or methidium azides are the preferred linking reagents. The nucleic acid component can be single or double stranded DNA or RNA or fragments thereof. The label can be anything which can be assayed in a known manner, for example, a hapten such as biotin, an enzyme such as $\beta$-galactosidase, alkaline phosphatase, horse radish peroxidase, papain or a phycobiliprotein.

Application Ser. No. 612,984, filed May 23, 1984 the disclosure of which is incorporated herein by reference, discloses a detection probe comprising a particular oligo or polynucleotide sequence, enzymatically coupled at one end to a nucleotide which contains a readable label. The coupled nucleotide can be a polyribonucleotide coupled to the 5' end of the oligo or polynucleotide probe by an enzyme such as T4 RNA ligase and can be directly readable. Alternatively, the nucleotide can be coupled to the 3' end by a terminal deoxynucleotidyl transferase. If the nucleotide is a triphosphate such as etheno ATP or CTP, the nucleotide triphosphate will be fluorescent and therefore, directly readable. The nucleotide triphosphate can contain a Hg or SH radical on the purine or pyrimidine ring, which can be read chemically or preferably could be further labeled, for example, with a hapten, fluorophore or enzyme. Although the invention is preferably employed for detection probes in hybridization assays, it can also be employed in immunological assays.

Application Ser. No. 582,503, filed Feb. 22, 1984, the disclosure of which is also incorporated herein by reference, discloses a nucleic acid probe coupled to a solid support via a single chemical covalent linkage. A specific embodiment of the invention entails the conjugation of a solid support containing a reactive $NH_2$ group to the nucleic acid, to yield a nucleic acid joined to a solid support via an amine linkage.

It is accordingly an object of the present invention to provide a highly convenient and sensitive immunoassay which is nonradioactive.

It is another object of the invention to provide a means of labeling immunological reagents with multiple labels, i.e., 20 or more labels per protein molecule, resulting in an immunoassay which is highly sensitive, e.g., as sensitive as radioimmunoassay.

It is another object of the invention to label the immunological reagent in such way that there is no interference with the immunological reaction.

These and other objects and advantages are realized in accordance with the present invention pursuant to which there is provided a protein covalently coupled to one end of a nucleic acid. The nucleic acid is the label carrier. Since polynucleotides can be covalently modified to carry large numbers of fluorescent and immunogenic molecules, they serve as a matrix for multiple labeling. A nucleic acid molecule is heavily labeled with, for example, a fluorescent molecule or hapten. Then, the labeled nucleic acid is covalently linked to a protein, for example, protein A.

The covalently coupled protein-nucleic acid can carry a large number of labels, on the nucleic acid, advantageously applied before the covalent coupling and before use of the coupled material in an immunoassay.

The labels may be of any known type, e.g., a fluorophore, an antigen, a hapten, an enzyme, a radioactive isotope, a cofactor or a carbohydrate.

In use, the protein moiety of the coupled material is specific for some other reagent such as another protein, a specific nucleotide sequence of a nucleic acid, as, for example, repressor proteins or a hapten, which latter can be detected by a secondary reaction with anti-hapten antibodies. Through this specificity, in effect, the labels become "attached" to the site to which the protein specifically binds.

The invention also extends to the process of conducting an assay for an antigen, as determined by the presence of a label, wherein an antigen, if contained in a sample, is complexed with an antibody. The antigen-antibody complex is then bound to a labeled protein through a link between the antibody and the labeled protein. This immunoassay is an improvement over prior immunoassays in that the nucleic acid, which is covalently coupled at one end to a protein, carries the label to be detected by the assay.

The invention also extends to a radioimmunoassay procedure wherein an antigen which may be present in a sample is complexed with an antibody specific for said antigen, the complex is bound to a covalently coupled protein-nucleic acid, as hereinabove described, and the nucleic acid portion is thereafter radioactively labeled and the label assayed.

Describing the invention in greater detail, the protein component can be of many diverse kinds, provided it is site specific. Particularly suitable materials include immunoglobulins, protein A, and the like. Protein A is a 40,000 Dalton single chain polypeptide isolated from *Staphylococcus aureus.* In some strains of *S. aureus,* it is covalently linked to the peptidoglycan part of the cell wall. Protein A binds to several IgG classes of antibodies through Fc-binding regions. In this case, the antibodies are specific for the antigen to be detected in the test sample. Protein A is very stable to heat and denaturing agents and can be renatured following denaturing conditions. [Review: J. W. Goding: Use of Staphylococcal Protein A as an immunological reagent, J. Imm. Methods 20 241-253 (1978)]. The binding of Protein A to IgG does not affect the antigen binding site of the IgG molecule.

Alternatively, the protein moiety can be an antibody such as IgG and will thus be specific for some antigen in the test sample. The antigen can be soluble, intrinsically or chemically bound to a cell surface or particulate substance. In general, all antigens can be detected using the NAPA reagents.

The diagnostic antigens which may be detected in an unknown sample include lymphocyte markers, tumor specific antigens, tumor cell markers, membrane receptors, microbial antigens, antigens representative of blood types and histocompatibility types, and antigens in serum, urine, etc., which are either elevated or depressed in various disease states.

The antibody has the specificity for a particular antigen. The antibody can be either monoclonal or polyclonal and can be one or more types, e.g., IgG, IgM, and the like. The antibody can be produced in vivo by a number of species or in vitro by cell culture or recombinant DNA technology.

The nucleic acid can be single or double stranded DNA, RNA, DNA-RNA hybrid, oligoribonucleotide or oligodeoxyribonucleotide.

The protein can be covalently coupled to the nucleic acid in various ways. In one procedure, one end of the nucleic acid is modified as with a terminal transferase so as to establish a ribonucleotide end, if not already present. The ribonucleotide end can be oxidized with periodate to form terminal aldehyde groups which can undergo a Schiff's base reaction with an amino-group of the protein, followed by hydrogenation to form a stable aminomethyl linkage between the protein and nucleic acid.

The label can be applied to the nucleic acid moiety before or after coupling to the protein and even at a much later stage in the assay. Because of its presence on the nucleic acid, the label will not interfere with the reactions of the protein moiety even though many labels may be present per protein moiety, e.g., 20 to 100 or even more. It has been previously shown that if certain proteins are directly labeled, as few as 6 labels are enough to interfere with the reaction.

The label can be attached to the nucleic acid as described in detail in application Ser. No. 513,932 and application Ser. No. 612,984, filed May 23, 1984 supra. Representative labels include fluorophores, for example, fluorescein, texas red, rhodamine or phycoerythrine; a hapten or antigen which can serve as a target for secondary labeled antibody; biotin which can be detected by labeled avidin or antibiotin antibody; an enzyme such as horseradish peroxidase or β-galactosidase assayed in a conventional manner; a cofactor for luminescent assay such as FAD or β-galactosidase; a fluorescent modification reagent which effects energy transfer or quenching; a radioisotope; or a carbohydrate.

As noted, the protein moiety should be site specific, as for example, to the Fc portion of an antibody such as IgG.

If the label of the NAPA complex is a fluorophore, the presence of the antigen, which reacts with the IgG-NAPA complex, can be determined by direct fluoroimmunoassay. If the label is a hapten, secondary amplification is necessary wherein an IgG molecule specific for the hapten is used. If the label is an enzyme, an enzyme assay can be used by which the amount of bound enzyme can be determined by the enzyme's catalytic reaction of its substrate in a known manner. If the label is a radioisotope, radioimmunoassay is performed in a conventional manner. In the case of a secondary amplification with an IgG specific for the label of the primary NAPA complex, read-out can be accomplished by addition of a second labeled NAPA complex carrying a different label.

The covalently coupled protein-nucleic acid can be used in immunoassays in a conventional manner, the labels either being present initially or being added at any stage prior to final assay.

Figure 2:
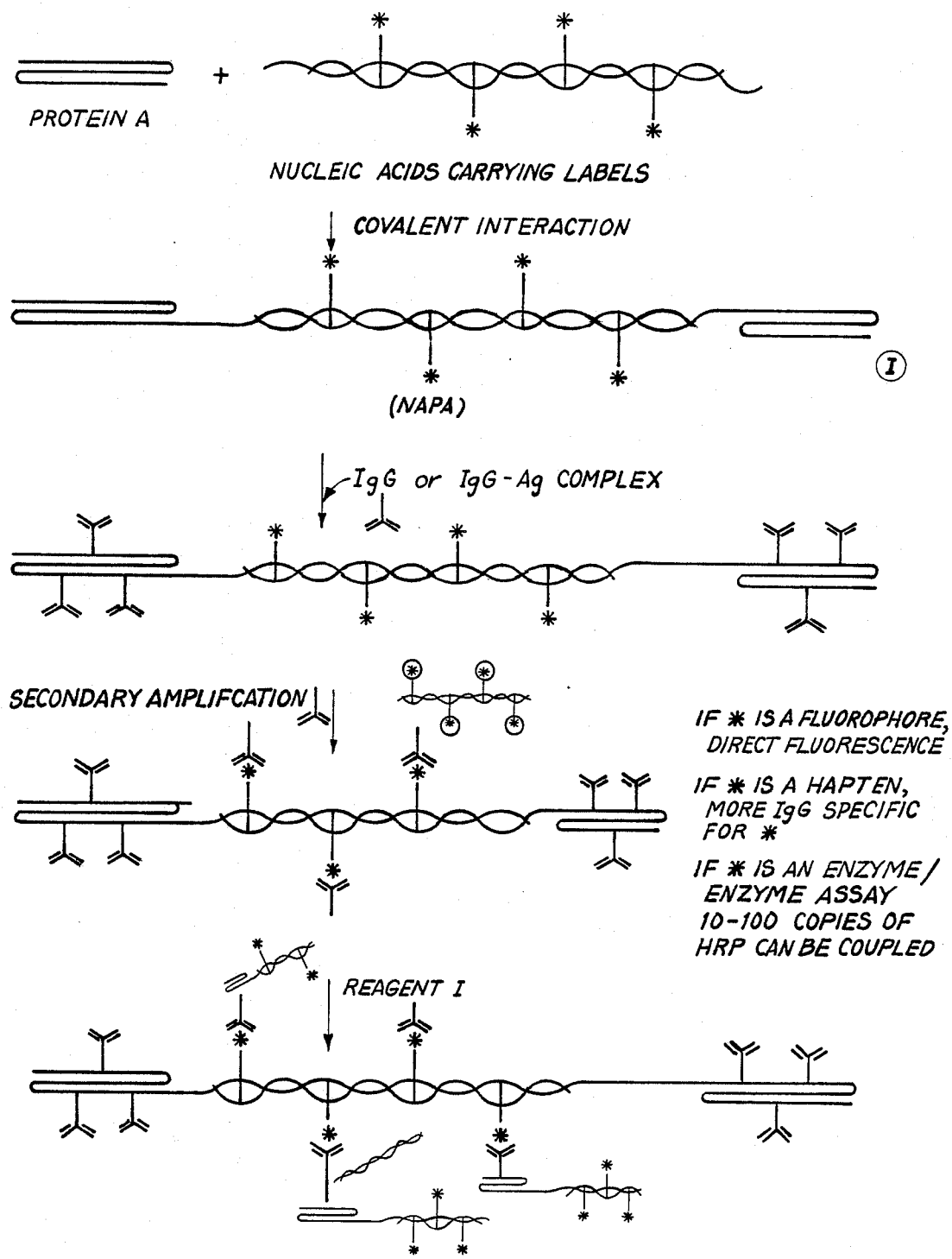

The invention will now be described in further detail with reference to the accompanying drawings wherein:

FIG. 1 is a schematic flowsheet of a process for coupling Protein A or IgG to a nucleic acid in accordance with one embodiment of the invention; and FIG. 2 is a schematic flowsheet of a method of using a coupled product of FIG. 1 in an assay.

Referring now more particularly to the drawings, in FIG. 1 a nucleic acid containing a terminal ribose residue (NA$_r$) is covalently linked to a ligand which binds nucleic acids, by photochemical methods (h$\nu$). If the NA$_r$ is DNA, the NA$_r$ is prepared from TdT-ATP (terminal deoxynucleotidyl transferase-adenosine triphosphate). If the NA$_r$ is RNA, it is used as such. The covalent adduct, (NA$_r$)ligand, is formed. The photo-chemical method employs, for example, a photoreactive ethidium azide or psoralen derivative as described in application Ser. No. 513,932, supra. If aminomethyl psoralens such as aminomethyltrioxsalen (AMT) or aminomethyl dimethyl-angelicin (AMA) are used, secondary labeling with fluorescein isothiocyanate (FITC) is possible. The adduct, for example, (NA$_r$)Ligand-Label, is formed which, by oxidation with periodate (NaIO$_4$), forms aldehyde groups

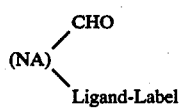

I

This complex, (1), reacts with Protein A and is reduced at (2) with NaBH$_4$ to form the NAPA complex

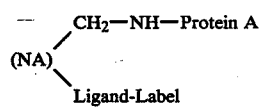

(3)

If, instead of Protein A the complex (1) reacts with IgG, and is reduced at (2), NA-IgG forms

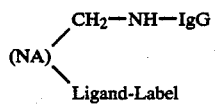

(3)

In place of the fluorescein label, other labels such as haptens, enzymes, cofactors, antigens, radioactive isotopes, carbohydrates and other fluorophores, can be similarly employed.

Referring more particularly to FIG. 2, Protein A is covalently coupled to the ends of a nucleic acid which carries several labels. The nucleic acid can be a single or double stranded DNA, RNA, DNA-RNA hybrid, oligoribonucleotide or deoxyribonucleotide.

The labelled Protein A-DNA adduct (NAPA) will react with an IgG or an IgG-antigen complex. The complex can then be assayed in conventional manner.

If one desires further amplification, however, the foregoing complex is reacted with an antibody specific for the labels, leaving the Fc fragments of the antibodies free to bind additional quantities of NAPA (Reagent I). This can then be assayed as before.

The invention will be further described in the following illustrative examples wherein all parts are by weight unless otherwise expressed.

EXAMPLE 1

Terminal transferase reaction to couple ribose residue at the end of DNA

Hae III digest of QX 174 RF or the product of Example 3 is dialyzed against potassium cacodylate buffer (pH 7.2; 200 mM) and the concentration is adjusted to $10^{-4}$ M in base pairs. To the DNA solution (100 $\mu$l), 5 $\mu$l 2 mM dithiothreitol 1 $\mu$l 10 mM ATP mixed with $^{14}$C labeled ATP and 10 $\mu$l 10 mM cobalt chloride are added. The mixture is incubated at 37° C. for 5 minutes and then chilled in ice for 10 minutes. 15 units of terminal deoxynucleotidyl transferase is added and the mixture incubated at 15° C. for 60 minutes. After the reaction, the enzyme is removed by phenol extraction and the unreacted nucleotides are removed by dialysis or passage through a Sephadex G-50 column. The yield is calculated from the absorbance to CPM ratio. Assuming uniform reaction, the yield is about 10-20 ATP residues per 3' end of the DNA. (For RNA-DNA hybrid or double stranded RNA, this step of TdT reaction is not required for further reaction.)

EXAMPLE 2

Oxidation and coupling of proteins

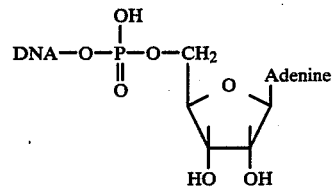

0.1 M sodium acetate
pH 5; 0.1 volume 1 M
sodium periodate

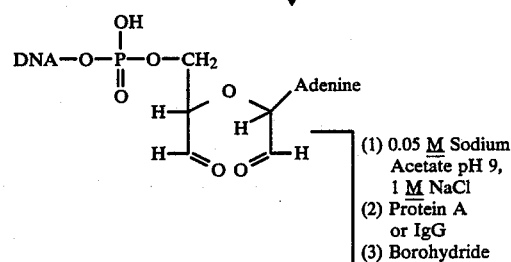

(1) 0.05 M Sodium Acetate pH 9, 1 M NaCl
(2) Protein A or IgG
(3) Borohydride reduction

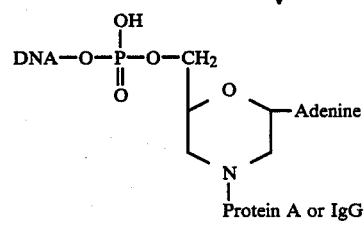

The oxidation of the ribose end of the product of Example 1 is effected with sodium periodate at room temperature using 0.1 M sodium acetate buffer pH 5 and 0.1 volume 1 M sodium periodate. The resulting solution is dialyzed to remove excess periodate against 1 M NaCl, 0.05 M sodium acetate pH 9. Then Protein A or IgG is added and the solution is reduced by adding Na-borohydride.

The reaction can be carried out between 0°–50° C. and in ionic strength up to 1 M NaCl.

EXAMPLE 3

Covalent reaction between double stranded nucleic acids and aminomethyl trioxsalen Hae III restriction enzyme digest of QX174 RF double stranded DNA or the product of Example 1 is dissolved in or dialyzed against Tris-EDTA buffer (TE) (10 mM trishydroxymethyl aminomethane, 1 mM EDTA; pH 7.1 adjusted with HCl). The concentration is adjusted to $1.5 \times 10^{-4}$ M/l in base pairs. 4'-aminomethyl trioxsalen dissolved in TE is added so that the ratio between the ligand to base pairs is 0.1. The mixture is flushed with nitrogen gas for 15 seconds and irradiated at 360 nm radiation for 60 minutes. This causes the trioxsalen residues to bind the DNA covalently. After the reaction, the mixture is precipitated with ethanol after adding sodium acetate to raise the ionic strength. The precipication also leaves any unreacted trioxsalen in the supernatant. By using tritiated trioxsalens, the relative amount of coupling can be estimated. (Exactly identical conditions can be employed for double stranded RNA and RNA-DNA hybrids).

EXAMPLE 4

Labeling of products of Example 2 and 3

The products of Examples 2 and 3 have free primary $NH_2$ residues from AMT and/or protein. They are reacted with biotin and/or fluorescein or rhodamine. An example is provided with fluorescein. A fluorescein isothiocyanate (FITC) solution is prepared by dissolving 5 mg of the solid in 2 ml ethanol. Products of Examples 2 and 3 are dialyzed again or dissolved in 0.1 M sodium bicarbonate buffer (pH 8–9). Then they are mixed with ethanolic solution of FITC in 15:1 volume ratio with equal weight concentration. The reaction is allowed to proceed for one hour. The product is purified on Sephadex G50 column. The excluded volume fractions contain the product. Labeling with biotin is done by using N-hydroxysuccinimido biotin as described in application Ser. No. 513,932, filed July 14, 1983, now pending.

EXAMPLE 5

Polyallylamino uridine phosphate (produced by enzymatic polymerization of allylamino uridine triphosphate in conventional manner) is reacted with fluorescein, rhodamine or biotin, as in Example 4, then reacted with protein as in Example 2.

The order of reactions can be changed, e.g., DNA can be reacted first with AMT, then ribose residue can be added by TdT, all AMT amine residues can be reacted with labels, and then coupling via redox reaction with proteins can be carried out.

EXAMPLE 6

For detection of tumor-specific antigen-carcinoembryonic antigen (CEA)

CEA is a glycoprotein and quantitation of serum CEA has been shown to have a prognostic and potentially diagnostic value in patients with ovarian, breast and colonic carcinoma.

A serum sample (0.1–1 ml) is incubated in a support (e.g., nitrocellulose) so as to allow coupling of the CEA to such a support. The coupling may be non-specific, e.g., adsorption of protein to plastic or may be specific, e.g., immobilization of CEA to a support using an antibody or Fab fragment specific for CEA, the antibody or fragment having been previously immobilized on this support.

The immobilized CEA is then incubated with a polyclonal antibody (selected for its antigenic specificity and Protein A binding characteristics and titrated to give maximum specific binding to the antigen) for 30 minutes at room temperature. Non-bound protein is removed by washing three times in phosphate buffered saline (20 mM sodium phosphate, 130 mM NaCl), containing 0.05% Tween-20 (PBS-Tw).

The fluorescein-labeled DNA-Protein A complex is incubated with the antibody-antigen complex for 30 minutes at room temperature and washed three times with PBS-Tw to remove non-bound NAPA complex.

The label is then assayed by fluorescent microscopy.

EXAMPLE 7

Analysis of histocompatability types

Lymphocytes are separated from whole blood (1 ml) using a Ficoll hypaque gradient. Lymphocytes are incubated in a battery of antisera, each antiserum specific for a particular histocompatability (HLA) sub-type. Non-bound antisera are removed by differential centrifugation and the cells washed three times using PBS. The washed lymphocytes are incubated with the fluorescein-labeled Protein A-DNA complexes. Non-bound fluorescein-labeled Protein A-DNA complexes are removed by differential centrifugation. The lymphocytes are then analyzed by fluorescent microscopy.

It is understood that the specification and examples are illustrative but not limitative of the present invention and that other embodiments within the spirit and scope of the invention will suggest themselves to those skilled in the art.

What is claimed is:

1. An assay for detecting an antigen comprising:
   combining a sample suspected of containing an antigen with an antibody specific to said antigen and a protein selected from the group consisting of Protein A and an antibody, said protein coupled to a 3' terminal end of a nucleic acid wherein the nucleic acid carries one or more label molecules;
   allowing complexation of said antigen, if contained in the sample, antibody and protein;
   incubating the resultant complex, and
   assaying for the label which is indicative of the amount of antigen in the sample.

2. An assay according to calim 1, wherein the nucleic acid is single or double stranded RNA or DNA, or a RNA-DNA hybrid.

3. An assay according to claim 1, wherein the label carried by the nucleic acid is selected from the group consisting of a fluorescent moiety, and antigen, a hapten, an enzyme, a radioactive isotope, a cofactor and a carbohydrate.

* * * * *

UNITED STATES PATENT AND TRADEMARK OFFICE
CERTIFICATE OF CORRECTION

PATENT NO. : 4,748,111

DATED : May 31, 1988

INVENTOR(S) : Nanibhushan Dattagupta, et al

It is certified that error appears in the above-identified patent and that said Letters Patent is hereby corrected as shown below:

| | |
|---|---|
| Title Page, Abstract, line 5 | Delete "FC" and substitute --Fc-- |
| Col. 1, line 11 | Delete "fdreign" and substitute --foreign-- |
| Col. 1, line 61 | Before "label" delete "bf" and substitute --of-- |
| Col. 6, line 10 | Insert space between "µl" and "10" |
| Col. 6, lines 65, 66, 67, 68; Col. 7, lines 4, 38 | Delete "M" and substitute --$\underline{\underline{M}}$-- |
| Col. 8, line 47 | After "protein" insert --capable of binding to said antibody, said protein-- |
| Col. 8, line 56 | Correct spelling of --claim-- |
| Col. 8, line 61 | Before "antigen" delete "and" and substitute --an-- |

Signed and Sealed this

Twenty-fourth Day of January, 1989

Attest:

DONALD J. QUIGG

Attesting Officer

Commissioner of Patents and Trademarks